United States Patent [19]

Scholl, Jr.

[11] Patent Number: 4,886,497

[45] Date of Patent: Dec. 12, 1989

[54] DISPOSABLE PROTECTIVE CONTAINER FOR HYPODERMIC SYRINGES

[76] Inventor: Charles W. Scholl, Jr., 23412 Via Alondra, Trabuco Canyon, Calif. 92678

[21] Appl. No.: 146,853

[22] Filed: Jan. 22, 1988

[51] Int. Cl.⁴ .............................................. A61M 5/00
[52] U.S. Cl. .................................... 604/111; 215/252
[58] Field of Search ................ 604/192, 263, 111; 215/250, 252, 253; 220/266, 265

[56] References Cited

U.S. PATENT DOCUMENTS

| | | | |
|---|---|---|---|
| 3,245,567 | 4/1966 | Knight | 604/263 X |
| 4,402,418 | 9/1983 | Ostrowsky | 215/252 |
| 4,479,586 | 10/1984 | Csaszar | 215/252 |
| 4,503,986 | 3/1985 | Nixdorff et al. | 215/252 |
| 4,549,667 | 10/1985 | Dullabaum | 215/252 |

*Primary Examiner*—John D. Yasko

[57] ABSTRACT

A container for hypodermic syringes which provides a first, tamper-indicating sealed position for containing a sterilized syringe and a seocnd, lockingly closed position for storing and safely disposing of a used syringe is disclosed. The container includes an elongated hollow plastic tube having an integral end wall closing one end. The opposite open end of the tube flares out to form an enlarged cylindrical boss section. A concave plastic cap fits snugly over rear annular beads projecting readially outwards from the rear portion of the outer cylindrical wall of the boss. Ultrasonic welds between the outer circumferential surface of the rear annular beads, and the inner cylindrical surface of the cap are breakable by twisting the cap relative to the tube providing an audible and tactile indication that the container has not previously been opened. The cap has one or more axially disposed resilient tabs, each tab formed between a pair of slots extending axially inwards from the annular end wall of the cap. A larger diameter, front annular bead projecting radially outwards from the front portion of the boss section of the tube lockingly engages a groove in the inner surface of each resilient tab of the cap when the cap is pushed sufficiently far down on a tube, containing a used syringe, permitting the container and enclosed syringe to be safely transported to a disposal site.

20 Claims, 2 Drawing Sheets

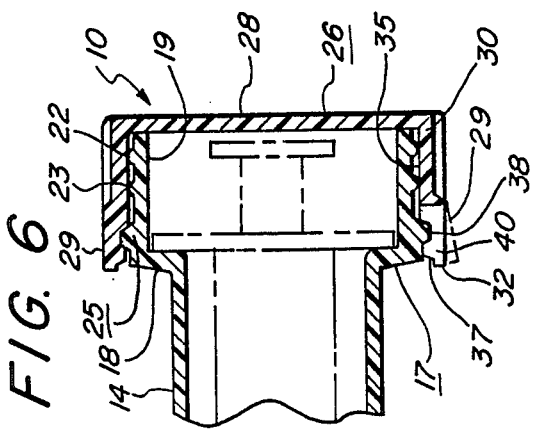
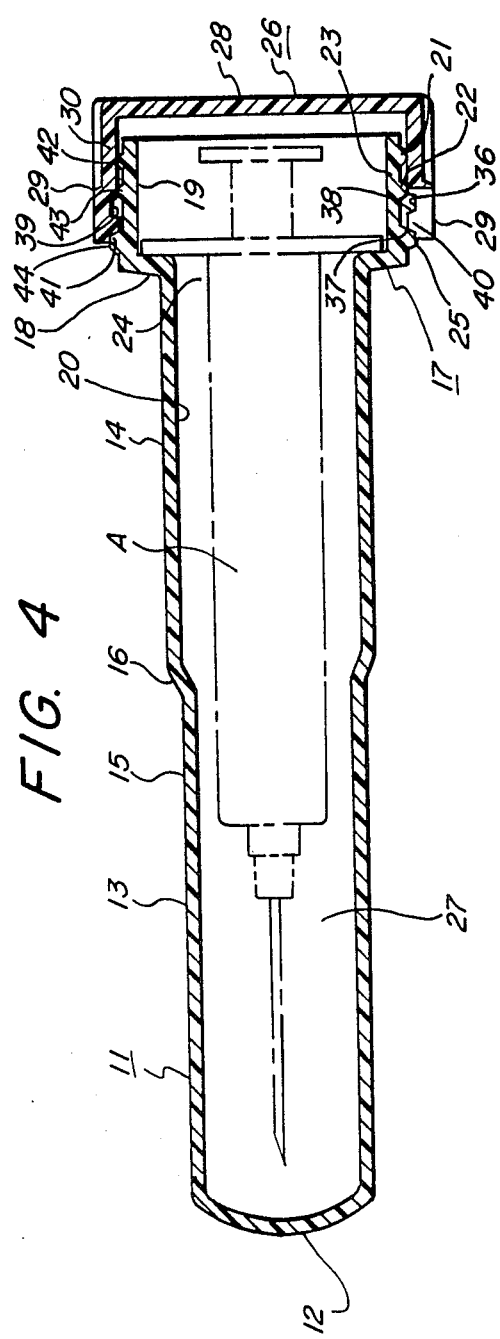
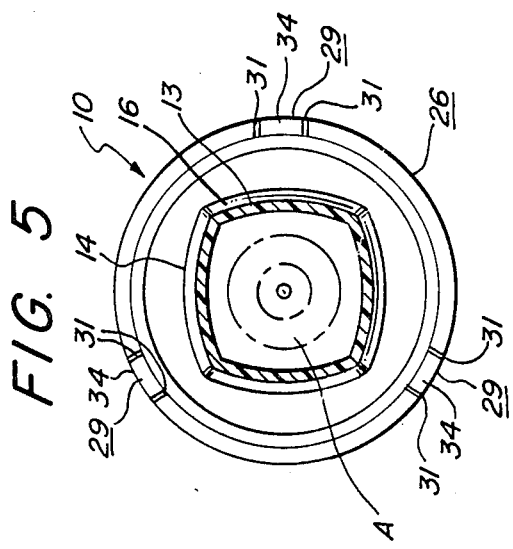

DISPOSABLE PROTECTIVE CONTAINER FOR HYPODERMIC SYRINGES

BACKGROUND OF THE INVENTION

A. Field of the Invention

The present invention relates to individual containers for hypodermic syringes. More particularly, the invention relates to a disposable container for hypodermic syringes which protects against inadvertent contact with the syringe needle before and after the syringe is used.

B. Discussion of Background Art

The use of hypodermic syringes has always posed a certain degree of risk to health care professionals, chiefly, doctors and nurses. Inadvertent contact with the sharp needle point by some part of the body of a person administering an injection can cause an unwanted injection of a drug contained in the syringe. However, since the amount of fluid which can be inadvertently injected is usually quite small, such accidental injections do not usually pose a serious health hazard.

A much greater hazard to users of hypodermic syringes is the potential contact with a needle that has been used to administer an injection or draw blood from a patient afflicted with a contagious disease. Accidental inoculation with a needle which has been used transcutaneously on a patient can result in the health care professional contracting a serious disease such as hepatitis.

Concern about the problem of accidental inoculation by a contaminated hypodermic syringe needle has increased along with the population growth and increased levels of health care usage of procedures involving hypodermic syringes. This concern has increased dramatically in the recent past, with the proliferation of individuals carrying the AIDS (Acquired Immune Deficiency Syndrome) virus. Bearing in mind that there is presently no known cure for this debilitating and deadly disease which has a 100% mortality rate, the high level of concern is well justified.

For the reasons stated above, there is a keen awareness among health care professionals of the necessity of taking substantial precautionary measures to avoid contacting a contaminated hypodermic syringe needle. Also, there is an awareness of the risk of using a hypodermic syringe which has been previously used or tampered with. These two concerns have prompted the development of a number of prior art devices intended to minimize the possibility of contacting a contaminated needle, or using a previously used or contaminated hypodermic syringe. Typical of such prior art protective devices are those disclosed in the following U.S. Pat. Nos.: Ogle, 3,272,322, Sept. 13, 1966, Syringe Package, which discloses a tamper indicating syringe package. Haller, 4,026,287, May 31, 1977, Syringe With Retractable Cannula, which discloses a syringe in which the cannula or needle may be withdrawn inside a protective barrel after use. Windischman, 4,106,622, Aug. 15, 1978, Tamper-Resistant Rigid Syringe Package And Method Of Making Same, which discloses a syringe package having a closure cap which visibly deforms if the cap is replaced on the closure, thereby indicating prior tampering. The cap may be replaced only with difficulty, and the package is therefore not designed to be re-used as a disposal unit. Mitchell, 4,631,057, Dec. 23, 1986, Shielded Needle, which discloses a hypodermic syringe with an integral telescopable shield, and Nelson, 4,659,330, Apr. 21, 1987, Hypodermic Syringe Needle Guard, which discloses an elongated protective needle guard cap for hypodermic syringes which has a flexible extension arm to keep the hands well away from the needle when replacing the cap on the needle.

The present invention was devised to provide a reusable tamper resistant package for hypodermic syringes in which a contaminated needle and syringe may be safely stored and disposed.

OBJECTS OF THE INVENTION

An object of the present invention is to provide a container for safely containing and transporting an individual hypodermic syringe before use, and for receiving, safely storing and disposing of a used syringe.

Another object of the invention is to provide a disposable protective package which will receive and store a standard hypodermic syringe.

Another object of the invention is to provide disposable protective package for a hypodermic syringe which provides a positive indication of the package having been previously opened.

Another object of the invention is to provide a disposable protective package for a hypodermic syringe which provides a positive indication of prior tampering, yet is easy to open.

Another object of the invention is to provide a disposable protective package for a hypodermic syringe which is re-closable to safely contain a used hypodermic syringe.

Another object of the invention is to provide a protective container for a hypodermic syringe which has an easily removable closure which may be replaced on the container in locking relationship with the container.

Various other objects and advantages of the present invention, and its most novel features, will become apparent to those skilled in the art by perusing the accompanying specifications, drawings and claims.

It is to be understood that although the invention disclosed herein is fully capable of achieving the objects and providing the advantages described, the characteristics of the invention described herein are merely illustrative of the preferred embodiment. Accordingly, I do not intend that the scope of my exclusive rights and privileges in the invention be limited to details of the embodiment described. I do intend that reasonable equivalents, adaptations and modifications of the invention described herein be included within the scope of the invention as defined by the appended claims.

SUMMARY OF THE INVENTION

Briefly stated, the present invention comprehends an improved design for a protective container for hypodermic syringes which also serves as a protective disposable container for syringes. The novel protective container according to the present invention includes an elongated plastic cylinder sealed at one end, adapted to coaxially contain a hypodermic syringe including a needle extending from one end thereof. A concave plastic cap located coaxially over the open end of the cylinder is welded to the outer annular wall of the cylinder. To obtain access to the hypodermic syringe, the cap must be twisted with respect to the cylinder, breaking the weld and providing a positive audible and tactile indication that the enclosed syringe has not been previously used or tampered with.

After use, the hypodermic syringe is reinserted into the cylinder. The cap contains in its cylindrical wall one or more axially disposed, flexible tabs formed between slots cut axially inward from the annular end wall of the cap surrounding its open end. Thus, when the cap is pushed axially downward over the open end of the cylinder sufficiently far for a bevelled skirt provided on each tab to slide over an annular bead provided on the cylinder, the bead lockingly engages an annular groove provided in the cap inwards from the bottom edge of the skirt. With the cap thus locked to the cylinder, the used hypodermic syringe is securely enclosed in the container, permitting safe transport of the container and enclosed syringe to a disposal site.

BRIEF DESCRIPTION OF THE DRAWINGS

FIG. 4 is a second transverse sectional view of the article of FIG. 1, taken along line 4—4.

FIG. 5 is a longitudinal sectional view of the container of FIG. 1, taken along line 5—5.

FIG. 6 is a fragmentary longitudinal sectional view of the article of FIG. 1, similar to FIG. 5 but showing a cap comprising one part of the container in a locked position.

DESCRIPTION OF THE PREFERRED EMBODIMENT

Referring now to FIGS. 1 through 6, and especially to FIGS. 1 through 5, a disposable protective container for hypodermic syringes according to the present invention is shown. The container 10 includes an elongated hollow plastic cylinder 11 sealed at one end by an integral convex end wall 12. As may be seen best by referring to FIGS. 1, 3 and 4, the cylinder 11 has a generally square transverse cross-sectional shape, the sides of the "square" being, however, bowed outward to present a generally convex perimeter.

Figure 1:
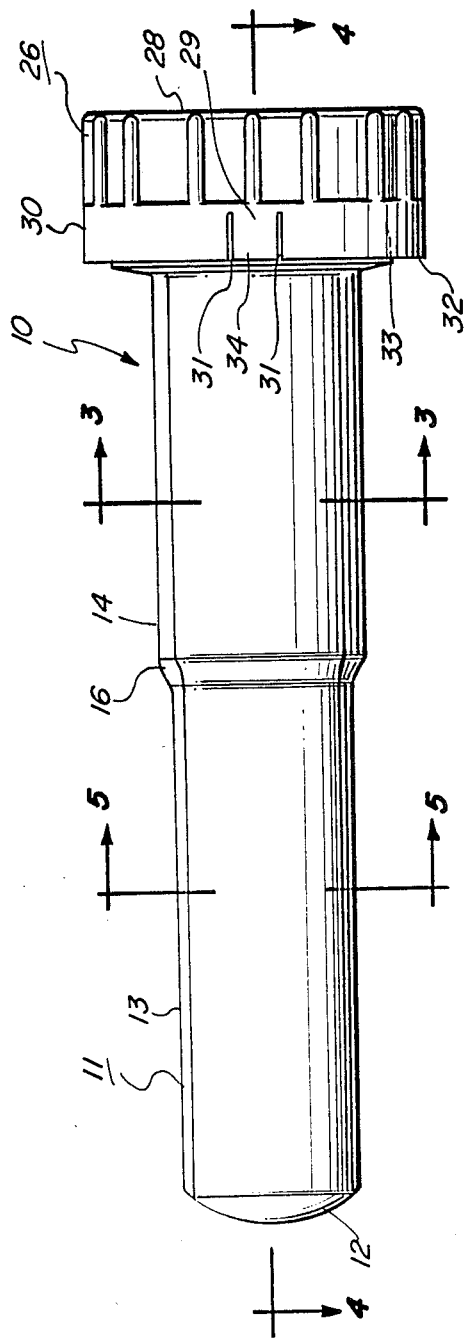
FIG. 1 is a side elevation view of a disposable protective container for hypodermic syringes according to the present invention.
Figure 3:
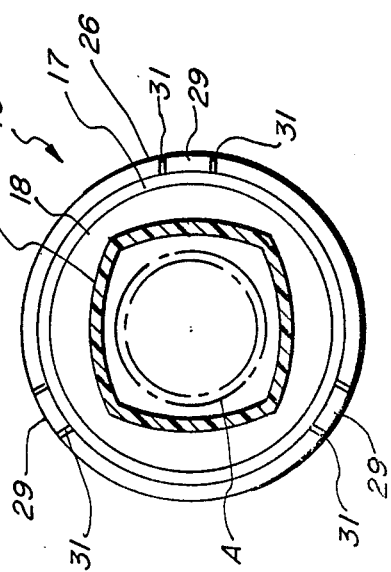
FIG. 3 is a first transverse sectional view of the container of FIG. 1, taken along line 3—3.

As shown in FIGS. 1 and 3, the front portion 13 of the cylinder 11, extending rearward from the front end wall 12, has a generally uniform inner diameter adapted to longitudinally receive the front barrel portion of a standard hypodermic syringe.

As may be seen best by referring to FIGS. 1 and 4, a rear longitudinal portion 14 of cylinder 11, comprising about one-half of the length of the cylinder, has a generally uniform inner diameter somewhat larger than the front portion 13. The front portion 13 and rear portion 14 of cylinder 11 are formed from a continuous longitudinal wall section 15 which has a tapered annular flange section 16 joining the front portions with the larger diameter rear portion.

As may be seen best by referring to FIGS. 1 and 5, the longitudinal wall section 15 of cylinder 11 forming the larger diameter rear portion 14 of the cylinder flares sharply outwards to form relatively short, enlarged diameter hollow boss section 17 joined to the rear end of the rear portion of the cylinder by substantially radially disposed annular flange section 18. The hollow boss section 17 has a smooth cylindrical inner wall surface 19 continuous with the inner wall surface 20 of the cylinder 11. A pair of annular beads 21 and 22 projects radially outwards from the outer cylindrical wall surface 23 of boss section 17. The rear annular bead 21 is spaced axially inwards a slight distance from the open rear end 24 of boss 17, while the intermediate annular bead 22 is spaced axially a slight distance inwards of the rear bead.

Boss section 17 also includes a front annular bead 25 projecting radially outwards from the outer cylindrical wall surface of the boss section. Front annular bead 25 is spaced axially forward of intermediate annular bead 23, just rearward of the annular flange section 18 joining the boss section 17 to the rear portion 14 of cylinder 11. The front annular bead 25 has a larger outer diameter than annular beads 21 and 22, and the purpose of each of these beads will be described below.

Cylinder 11, including each of its structural elements as described above, is preferably fabricated from a sterilizable plastic such as polypropylene by injection molding or blow molding.

Figure 2:
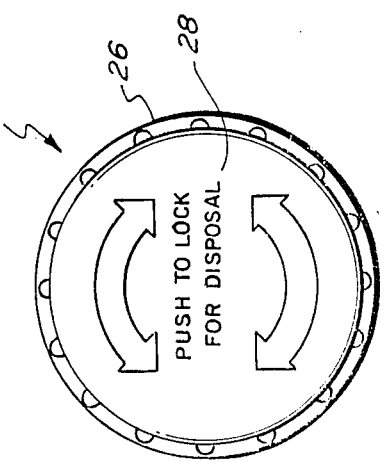
FIG. 2 is an end view of the container of FIG. 1.

As may be seen best by referring to FIGS. 1 and 2, the protective container 10 according to the present invention includes a hollow cylindrical cap 26 adapted to fit coaxially over hollow rear boss section 17 of cylinder 11, closing off the interior space 27 of the cylinder forward of the disc-shaped end wall 28 of the cap. Cap 26 is preferably injection molded from a sterilizable resilient plastic material such as polypropylene.

The cap 26 includes a plurality, preferably three, of snap locks 29 formed in the cylindrical wall 30 of the cap. These snap locks are spaced at equal distances circumferentially around the wall of the cap. The snap locks 29 are each formed by a pair of thin, axially disposed slots or kerfs 31 piercing the cylindrical wall 30 of the cap 26. Each of the slots 31 in a pair is parallel to one another, and extends inwards a short distance from the annular end wall 32 surrounding the open end 33 of the cap 21. The slots 31 in a pair are spaced relatively close to one another, leaving an axially elongated relatively narrow rectangular tab 34 between each pair of slots.

As may be seen best by referring to FIGS. 5 and 6, the inner cylindrical wall surface 35 of tabs 34 each contains an axially aligned annular groove 36 a short distance inwards from the annular end wall 32 of the cap 26. The annular end wall 32 of the cap 26 is bevelled to form a gently sloping cam surface 37 joining the inner cylindrical wall surface 35 of tab 34. A slight distance axially inwards from the intersection of cam surface 37 with cylindrical wall surface 35 of tab 34, a steeply sloping surface 38 extends radially outwards to the bottom wall 39 of annular groove 36, forming the front wall surface of the groove. The gently sloping cam surface 37, steeply sloping front wall surface 38, and the portion of the inner cylindrical wall surface 35 of tab 34 form together a radially inwardly projecting locking bead 40 which is a segment of a circle common to each of the plurality of tabs 34.

The protective container 10 is used as follows. First, the cylinder 11 and cap 26 comprising the major components of the container 10 are sterilized. Next, as shown in FIG. 5, a sterilized hypodermic syringe A is inserted into the opening 24 in the rear boss section 17 of cylinder 11. Then, as shown in FIG. 5, cap 26 is placed coaxially over the rear boss section 17, and pushed down just far enough for the front cam surface 37 of tube 34 to abut the sloping rear surface 41 of front annular bead 25 projecting radially outwards from the boss section. Then the inner cylindrical wall surface 35 of cap 34 is welded to the outer circumferential surfaces 42 and 43 of rear and intermediate annular beads 21 and 22 projecting radially outwards from the boss section 17. Preferably, plastic cap 26 is fastened to boss section 17 of cylinder 11 by ultrasonic or radio frequency welding.

To gain access to a hypodermic syringe A packaged in container 10 as described above, cap 26 must be twisted relative to cylinder 11 to break the welds joining the cap to the boss section 17 of the cylinder. The breaking of the weld produces a distinctive snap which can both be heard and felt by the person opening the container, providing a positive indication that the hypodermic syringe contained in the package has not been previously used or tampered with. Conversely, the absence of the tactile and audible signal produced by the welds breaking warns the user of tampering or prior use.

After a hypodermic syringe has been removed from the container 10 in the manner described above, the container provides a novel and very effective means for safely storing and transporting to a disposal site a used hypodermic syringe, as will now be described.

Referring now to FIG. 5, a used syringe A is inserted into cylinder 11 and cap 26 pushed down over the rear boss section 17 of the cylinder exactly as has been described above. This time, however, the cap 26 is pushed further forward, to the extent that the bevelled front cam surface 37 on the front annular end wall 32 of each tab 34 slides upward on the abutting rear sloping surface 41 of the front annular bead 25 of the boss section 17. Radially outward movement of tabs 34 relative to the cylindrical wall 30 of the cap 26 is permitted by the flexibility of the plastic material from which the cap is made, and facilitated by slots 31 on either side of each tab.

As the cap 26 is pushed further downward over boss section 17, the radially inwardly projecting locking bead 40 of each tab 34 eventually slides over the radially outwardly projecting front annular bead 25 of the boss section 17. Pushing the cap 26 slightly further down on the boss section 17 causes locking bead 40 to seat in the annular groove 36 of each tab 34, the elasticity of the tab restoring it to its original position from its radially outwardly distorted position. In this seated position, the steeply sloping front wall surface 38 of the annular groove 36 in each tab 34 abuts the front wall surface 44 of front annular bead 25 of boss section 17. Contact between these two abutting surfaces prevents rearward axial movement of the cap 26 relative to the cylinder 11, after the cap has been pushed all the way down on the boss section 17 to snappingly engage bead 25 of the boss section in grooves 36 of the tabs 34 of the cap. With cap 26 and cylinder 11 thus lockingly engaged, the cap is securely locked to the cylinder. Since more force than is exertable by a normal human being would be required to pull off cap 26 from cylinder 11 once they are lockingly engaged as described above, the container 10 and enclosed used hypodermic syringe A may be safely disposed of without the danger of contacting the potentially biologically hazardous needle of the used syringe.

What is claimed is:

1. A two piece container having a first, tamper indicative sealed position and a second, locking sealed position comprising:
   (a) an elongated hollow body having one sealed end and one open end,
   (b) a concave cap adapted to fit over said open end of said elongated hollow body,
   (c) frangible fastening means between the inner wall of said cap and the outer wall of said body, said frangible fastening means adapted to hold said cap in a first sealing position relative to said body, and
   (d) locking fastening means adapted to hold said cap in a second sealing position after breaking said frangible fastening means.

2. The container of claim 1 wherein said frangible fastening means is broken by rotation of said cap relative to said body about the longitudinal axis of said body.

3. The container of claim 2 wherein said locking fastening means is actuated by pushing said cap axially downward over said open end of said hollow body.

4. The container of claim 2 wherein said frangible fastening means provides a sound and vibration when broken, thereby providing an indication of said container not having been previously opened.

5. The container of claim 2 wherein said body and said cap are made of plastic.

6. The container of claim 5 wherein said frangible fastening means comprises a welded joint between said cap and said body.

7. A container for hypodermic syringes and the like having a first, tamper-indicating sealed position and a second, locking sealed position comprising:
   (a) an elongated, hollow cylindrical tube sealed at one end, and open at the other end,
   (b) a concave cap adapted to fit over said open end of said tube,
   (c) frangible fastening means joining the inner wall of said cap to the outer cylindrical wall of said tube, said frangible fastening means adapted to hold said cap in a first axial position relative to said tube, and
   (d) locking fastening means adapted to hold said cap in a second axial position relative to said tube after breaking said frangible fastening means.

8. The container of claim 7 wherein said locking fastening means comprises in combination at least one elastically deformable member on said cap and a member on said tube lockingly engageable with said elastically deformable member.

9. The container of claim 8 wherein said locking fastening means is actuated by pushing said cap axially downward over said open end of said tube to said second axial position relative to said tube.

10. The container of claim 9 wherein said second axial position is closer to said closed end of said tube than said first axial position.

11. The container of claim 10 wherein said locking fastening means is further defined as a radially deformable section of the cylindrical wall of said cap comprising at least one axially elongated tab extending inward a short distance from the annular end wall of said cap surrounding its open end, slots being provided on either side of each tube to permit radial movement of said tab.

12. The container of claim 11 wherein said tab is provided with a radially inwardly projecting groove lockingly engageable with a radially outwardly projecting member on said tube.

13. The container of claim 12 wherein said tube and said cap are made of plastic.

14. The container of claim 13 wherein said frangible fastening means comprises a welded joint between the outer cylindrical wall of said tube and the inner cylindrical wall of said cap.

15. The container of claim 14 wherein said tube and said cap are made of polypropylene.

16. A two-piece container for hypodermic syringes having a first, tamper indicating sealed position and a second, locking sealed position comprising:
 (a) an elongated, hollow cylindrical tube having an integral front end wall sealing the distal end of said tube, and an enlarged hollow cylindrical boss section at the proximal end of said tube, said boss section having an annular bead projecting radially outwards from the front portion of the cylindrical wall section of said boss, and
 (b) a concave cap adapted to fit snugly over said boss section, said cap having a resilient cylindrical wall section containing on its inner surface a radially outwardly projecting annular groove adapted to lockingly engage said bead on said boss section.

17. The container of claim 16 wherein said resilient wall section is further defined as comprising at least one axially elongated tab extending inwards from the annular end wall of said cap surrounding its open end, axial slots being provided on either side each tab to permit radial movement of said tab.

18. The container of claim 17 further including at least one rear annular bead projecting radially outwards from the rear portion of the cylindrical wall section of said boss, said rear annular bead having a smaller diameter than said front annular bead and adapted to contact the inner cylindrical wall surface of said cap without deformation of said cap, thereby facilitating formation of a frangible joint between said cap and said boss.

19. The container of claim 18 wherein said cap and said cylinder are made of plastic.

20. The container of claim 19 wherein said frangible joint is a welded joint.

* * * * *